United States Patent [19]

Adamczyk et al.

[11] Patent Number: 5,100,807
[45] Date of Patent: Mar. 31, 1992

[54] PHENYLACETYLGLUTAMINE (PAG) ANALYTICAL TEST

[75] Inventors: Maciej B. Adamczyk, Lindenhurst; Hossein A. Ghanbari, Libertyville; Donald D. Johnson, Lindenhurst, all of Ill.

[73] Assignee: Abbott Laboratories, Abbott Park, Ill.

[21] Appl. No.: 110,155

[22] Filed: Oct. 19, 1987

[51] Int. Cl.$^5$ ............... G01N 33/566; G01N 33/531; A61K 35/14; C07D 311/82
[52] U.S. Cl. ...................... 436/543; 436/501; 436/544; 436/547; 436/822; 530/389.8; 530/323; 549/223
[58] Field of Search ............... 436/501, 543, 544, 546, 436/547, 822; 530/387, 389, 323; 549/223

[56] References Cited

U.S. PATENT DOCUMENTS

| | | | |
|---|---|---|---|
| 4,255,329 | 3/1981 | Ullman | 540/589 |
| 4,351,760 | 9/1982 | Khanna et al. | 530/395 |
| 4,420,568 | 12/1983 | Wang et al. | 436/536 |
| 4,476,228 | 10/1984 | Huchzermeier et al. | 436/500 |
| 4,476,229 | 10/1984 | Fino et al. | 436/500 |
| 4,481,136 | 11/1984 | Khanna et al. | 530/391 |
| 4,492,762 | 1/1985 | Wang et al. | 436/537 |
| 4,510,251 | 4/1985 | Kirkemo et al. | 436/536 |
| 4,558,057 | 12/1985 | Burzynski | 546/220 |
| 4,585,862 | 4/1986 | Wang et al. | 544/319 |
| 4,588,697 | 5/1986 | Khanna et al. | 436/518 |
| 4,593,089 | 6/1986 | Wang et al. | 536/13.6 |
| 4,681,859 | 7/1987 | Kramer | 436/501 |

FOREIGN PATENT DOCUMENTS 2111476A 7/1983 United Kingdom .

OTHER PUBLICATIONS

Nenasheva et al., *Chemical Abstracts*, vol. 96 (21):177270w, (1982).
Shipchandler et al., *Analytical Biochemistry*, 162:89-101 (1987).

*Primary Examiner*—Esther L. Kepplinger
*Assistant Examiner*—Janelle Graeter
*Attorney, Agent, or Firm*—Robert W. Stevenson; Daniel W. Collins; Thomas M. Breininger

[57] ABSTRACT

The present invention is directed to a fluorescence polarization immunoassay for determining the phenylacetylglutamine (PAG) content in body fluids, to the various components needed for preparing and carrying out such an assay, and to the methods of making these components. Specifically, tracers, immunogens and antibodies are disclosed, as well as methods for preparing them. The assay is conducted by measuring the degree of polarization of plane polarized light that has been passed through a solution continuing sample, antiserum and tracer.

10 Claims, 4 Drawing Sheets

PHENYLACETYLGLUTAMINE (PAG) ANALYTICAL TEST

BACKGROUND OF THE INVENTION

The present invention relates to immunoassays for detection of phenylacetylglutamine (PAG) content in body fluids, and to novel antibodies and fluorescein conjugates useful in assays to detect PAG.

According to the 2-phenylethylamine (PEA) theory of affective behavior, an increase in the brain level of PEA may underline mania while a relative deficit may play a major role in certain forms of depression. Since phenylacetic acid (PAA) is formed metabolically by oxidative deamination of PEA, and PAA is excreted with urine almost entirely in its conjugated form as PAG, assays for monitoring PAG can be useful in diagnosing or monitoring mania or depression.

Techniques previously employed to determine PAG levels in blood or urine involve hydrolyzing PAG to PAA. The PAA is then quantified by fluorometric procedures (A. A. Boulton, Progr. Neurogenetics, 1:937 (1967) or gas chromatography; K. Blau, Clin. Chim. Acta, 27:5-18 (1970); H. Curtius et al., Clin. Chim. Acta, 27:277-285 1972 ; Goodwin et al., Clin. Chim. Acta, 62:443 (1975); Davis et al., Journal of Chromatography, 222:161-169 1981 ; Fellows et al., Biochemical Mass Spectrometry, Vol. 5, No. 8 (1978); Markin et al., Analytical Biochemistry, 99:283-287 (1979). Such tests are extremely time consuming. Typically, only several samples can be analyzed in a day. In addition, the equipment used in such analysis is expensive, often several hundred thousand dollars if gas chromatography and mass spectrometry are used.

As indicated above, applicants developed a new fluorescence polarization immunoassay test for PAG. Typically, for endogenous substances (PAG being an endogenous substance in the patient), the incubation times required for FPIAs for endogenous substances typically take a number of minutes. Thus, the total analysis time for a given sample can take anywhere from twenty to one hundred twenty minutes.

SUMMARY OF THE INVENTION

Applicants discovered unexpectedly that in raising antibodies against PAG to use in an FPIA for PAG, the characteristics of the antibodies raised for use in the test were completely unexpected. The antibodies raised yielded a test which has incubation time of less than three minutes, thus the total analysis time for a sample is typically only above six minutes. In fact, Applicants found that they can analyze 20 samples in as little as thirteen minutes on an Abbott TDx analyzer. This is unexpected not only in view of Applicants prior experience in FPIAs, but also it is a remarkable reduction in the analysis time over the GC/mass spec analysis heretofore utilized.

The antibodies of the present invention are raised against a compound of formula I:

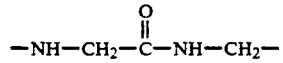

I wherein $R_1$ is a poly(amino)acid, preferably bovine serum albumin,

The present invention also includes fluorescein tracers of the structure of formula I wherein $R_1$ is fluorescein, or a fluorescein linked to the structure of formula I by a linker of the formula:

$$-NH-CH_2-\overset{O}{\overset{\|}{C}}-NH-CH_2-$$

Other aspects of the invention relate to methods of preparing such immunogens and tracers, and to a method of making PAG synthetically.

DETAILED DESCRIPTION OF THE INVENTION

Figure 1:
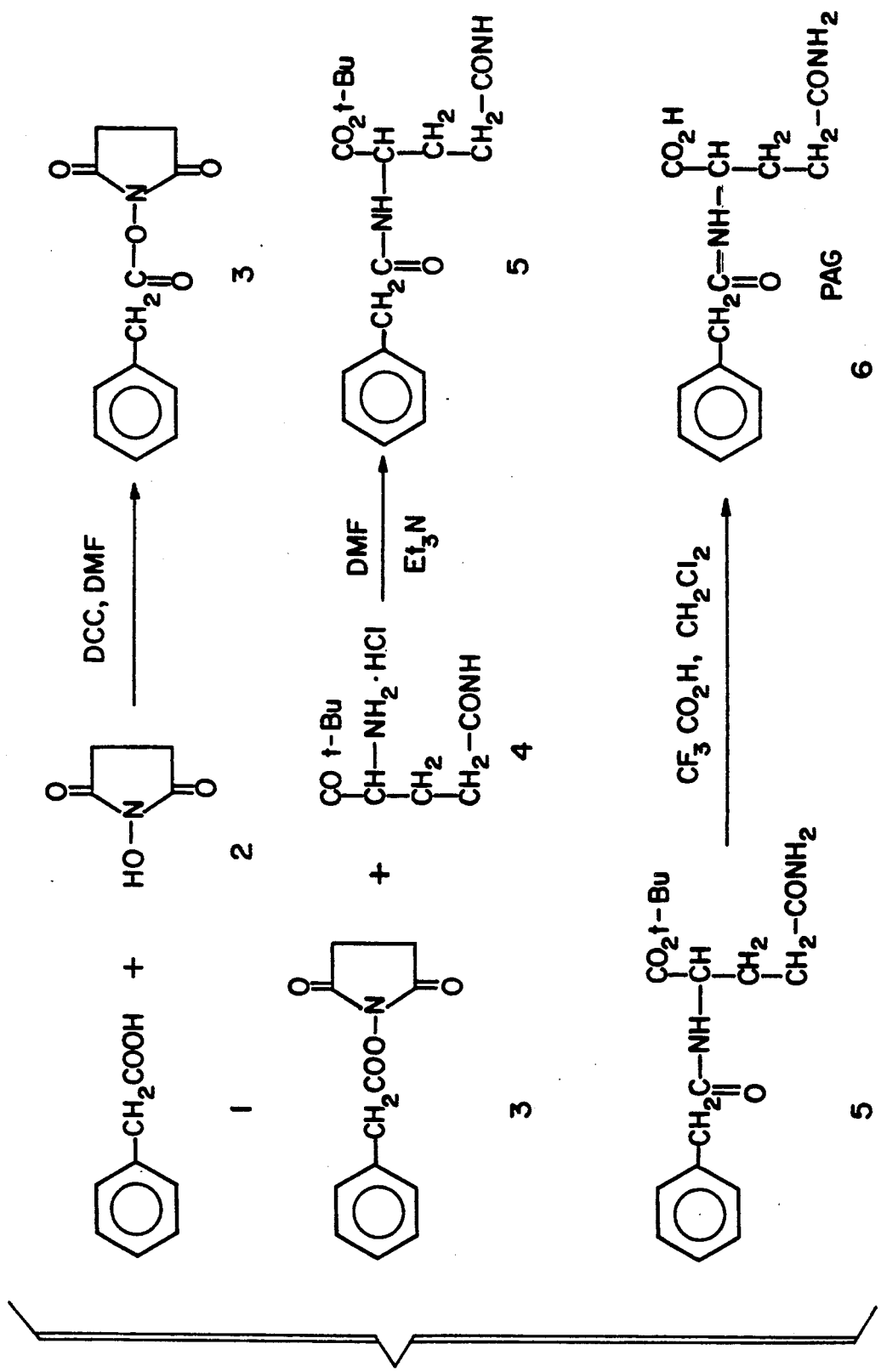
FIG. 1 illustrates the synthetic pathway for phenylacetylglutamine (PAG) according to the method of the present invention.

1. General The fluorescence polarization immunoassay (FPIA) of the present invention combines the specificity of an immunoassay with the speed and convenience of homogenous methods to offer precise and reliable procedures for monitoring PAG levels in urine or blood.

In an FPIA, the biological substance being measured (usually referred to as the "ligand") competes with the fluorophore labeled reagent (the "ligand analog" or "tracer") for a limited number of receptor binding sites on antibodies specific to the ligand and ligand analog. The concentration of ligand in the sample determines the amount of ligand analog which binds to the antibody. This general approach is described in Wang, et al., U.S. Pat. No. 4,420,568 which is incorporated herein by reference. The amount of ligand analog that will bind is inversely proportional to the concentration of ligand in the sample because the ligand and the ligand analog each bind to the antibody in proportion to their respective concentrations.

Fluorescence polarization may be utilized to measure the amount of tracer-antibody conjugate produced in a competitive binding immunoassay. Fluorescence polarization techniques are based on the principle that a fluorescent labelled compound, when excited by plane polarized light, will emit fluorescence having a degree of polarization inversely related to its rate of rotation. Accordingly, when a tracer-antibody conjugate having a fluorescent label is excited with plane polarized light, the light remains highly polarized because the fluophore is constrained from rotating between the time that light is absorbed and the time that it is emitted. In contrast, when an unbound tracer is excited by plan polarized light, its rotation is much faster than that of the corresponding tracer-antibody conjugate; as a result, the light emitted from the unbound tracer molecules is depolarized within the absorption-emission time lapse. The decrease in polarization is indicative of the amount of ligand in the sample.

Accordingly, the synthesis of immunogens and tracers, and the raising of antibodies for use in the present FPIA for PAG will be described below.

2. The Synthesis of Immunogens The immunogens of the present invention are made by coupling a hapten, such as shown by the structure of Formula I when $R^1$ is OH to a poly(amino acid) or other immunologically active carrier. The poly(amino acid) or other carrier moiety can be linked to the hapten by amido (peptide), carbamate, thioether, ether, diazo, or amino linkage. In a preferred embodiment, the poly(amino acid) is bovine serum albumin (BSA). These reactants are preferably coupled under conditions normally used to form amide linkages; such conditions are well known to those skilled in the art.

The immunogens are prepared by coupling a hapten that contains a CHO, carboxylic, amino, hydroxide, or an iodoacetonyl group to poly(amino acid) or other immunologically active carrier. The —CHO can be coupled by forming a Schiff's base which is instantly reduced by sodium cyano borohydride to form the stable aminomethyl linkage. The activation of the carboxylic groups on the hapten or on the poly(amino acid) can be accomplished by mixing the hapten and the poly(amino acid) with 1-ethyl-3-(3-dimethylamino-propyl) carbodiimide (EDC), N,N[1]-dicyclohexylcarbodiimide (DCC), 1-cyclohexyl-3-(2-morpholinoethyl)carbodiimide methyl-p-toluene sulfonate, or the like.

Specific examples of immunogen synthesis are provided in Examples 1 and 2.

3. The Synthesis of the Tracers The tracers of the present invention are made by coupling a fluorescein moiety or a derivative of fluorescein to a general structure shown in Formula I.

The fluorescein moiety can be linked to the amino, carboxyl, aldehyde, or acid chloride group by an amide, amine, an urea, carbamate, or triazinylamino linkage. In the presently preferred embodiment, the fluorescein derivative is aminomethylfluorescein which is coupled to PAG. PAG is coupled to aminomethyl fluorescein by first forming the active ester of its carboxylic group. The preferred active ester is N-hydroxysuccinimide active ester and the preferred method is via N,N[1]-dicyclohexylcarbodiimide activation. Other activating groups, such as acid chloride, 1-hydroxybenzotriazol, p-nitrophenol, 2-ethyl-5-phenylisoxazolium 3[1]sulfonate can be used.

Specific examples of tracer synthesis are provided in Examples 3 and 4.

4. Raising Antibodies The procedure for raising antibodies for use in the present invention involves injecting an animal, preferably a rabbit with an immunogen of this invention. The animal produces antibodies to the hapten, and the antibodies are collected by bleeding the immunized animals and isolating the serum. The collected serum is stored at $-20°$ C.

The preferred method of raising antibodies according to the present invention is disclosed in Example 5.

EXAMPLE 1

Synthesis of Phenylacetylglutamine (PAG)

As previously indicated, the present invention also relates to a novel method of synthesizing PAG. In its broadest aspects, this method involves coupling phenylacetic acid to a glutamine where the carboxylic acid moiety on the glutamine is protected with a carboxyl protecting group such as benzyl or t-butyl.[1] Then, after coupling, the carboxylic acid moiety is deprotected to produce PAG. ,6 [1] The term "carboxyl protecting group" is known in the art and includes benzyl, t-butyl, p-nitro phenyl, methyl and the like as described in T. Greene, Protective Groups In Organic Synthesis, John Wiley & Sons pp. 152-192 (1981).

As shown in reaction scheme I (FIG. 1), phenylacetic acid 1 (1250 mg; 1.84 mmol) was coupled to a protected glutamine 4 (protected in this case by a lower alkyl such as t-butyl group) by first dissolving the phenyl acetic acid in anhydrous dimethylformamide (8 ml). N-hydroxysuccinimide 2 (254 mg; 2.2 mmol) was added followed by addition of dicyclohexylcarbodiimide (456 mg; 2.2 mmol) to produce N-succinimidphenylacetate 3. The reaction mixture was stirred for ten hours and precipitated dicyclohexyl urea was filtered off. The filtrate containing 3 was returned to a reaction flask to which a carboxy-protected glutamine such as L-glutamine t-butyl-ester hydrochloride 4 (439 mg; 1.84 mmol) was added. pH was adjusted to 9 with triethylamine, and the reaction mixture was stirred for 24 hours to produce phenylacetylglutamine t-butyl ester 5. Precipitated crystals were filtered off, and the filtrate containing 5 after concentration in vacuum was purified by column chromatography on silica gel using ethyl acetate-methanol (95:5) as an eluent. Yield 299 mg of desired material, mp. $132°-133°$ C. $^1$H-NMR (60 MHz) (CDCl$_3$) δ ppm: 1.4 (s,9H); 1.8-2.4 (mult,4H); 3.6 (s,2H); 4.5 (mult,1H); 5.5 (broad,1H); 6.3 (mult,2H); 7.3 (s,5H). Mass Spectrum (DEI/DIP): 321 (M+H)+, 320 M+, 264 (M-C$_4$H$_8$)+, 247 (M-OC$_4$H$_9$)+. The t-butyl ester 5 (295 mg; 0.924 mmole) of phenylacetylglutamine was deprotected (i.e., the t-butyl carboxy protecting group was removed) by dissolving 5 in methylene chloride (4 ml) and adding trifluoroacetic acid (4 ml). After 45 minutes, the reaction mixture was evaporated in vacuum and the oily residue crystallized from tetrahydrofurane (THF), to give colorless crystals of phenylacetyl glutamine 6. $^1$H-NMR(300 MHz)(CDCl$_3$/CD$_3$OD) δ ppm 1.9-2.05 (mult,1H); 2.13-2.36 (mult,3H); 3.58 (s,2H); 4.5 (mult,1H); 7.23-7.38 (mult,5H); Mass Spectrum (pos.FAB, MeOH):265 (M+H)+ (100%).

Other methods of coupling phenyl acetic acid to a carboxy protected glutamine will be apparent to one of ordinary skill. Other carboxy protecting groups besides t-butyl will also be apparent.

EXAMPLE 2

Coupling of Phenylacetylglutamine to Bovin Serum Albumin

Figure 2:
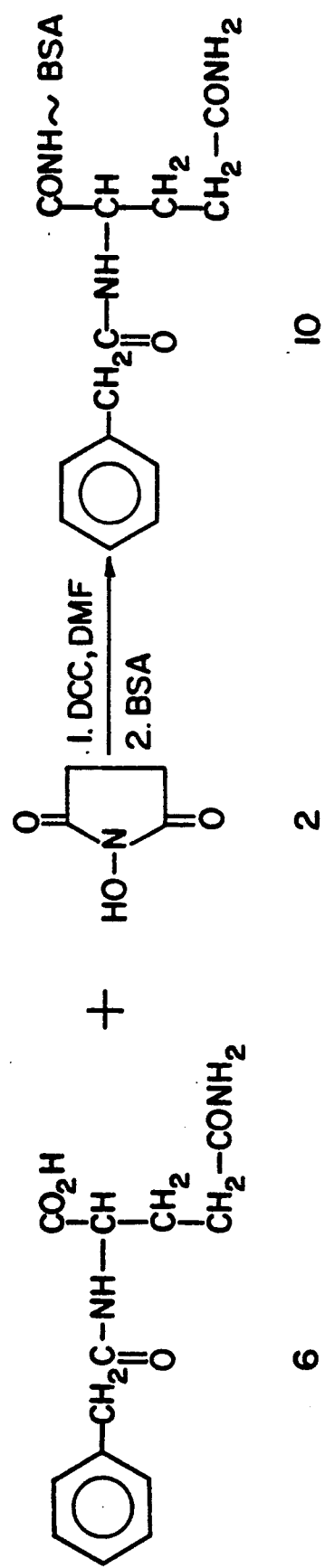
FIG. 2 illustrates the synthetic pathway for coupling PAG to bovine serum albumin according to the method of the present invention.

As shown in scheme II (FIG. 2), phenylacetylglutamine 6 (117 mg; 0.441 mmol was dissolved in dimethylformamide (1.8 ml , and N-hydroxysuccinimide 2 (61 mg; 0.529 mmol) was added followed by dicyclohexylcarbodiimide (109 mg; 0.529 mmole). After 12 hours bovine serum albumin (500 mg) dissolved in 0.1M phosphate buffer (10 ml; pH=7.8) was added, and the reaction mixture was stirred for additional 18 hours. The reaction mixture was dialized against water, and lyophilized to yield the immunogen conjugate 10 (502 mg).

EXAMPLE 3

Coupling of Phenylacetylglutamine (PAG) to Aminomethylfluorescein (AMF)

Figure 3:
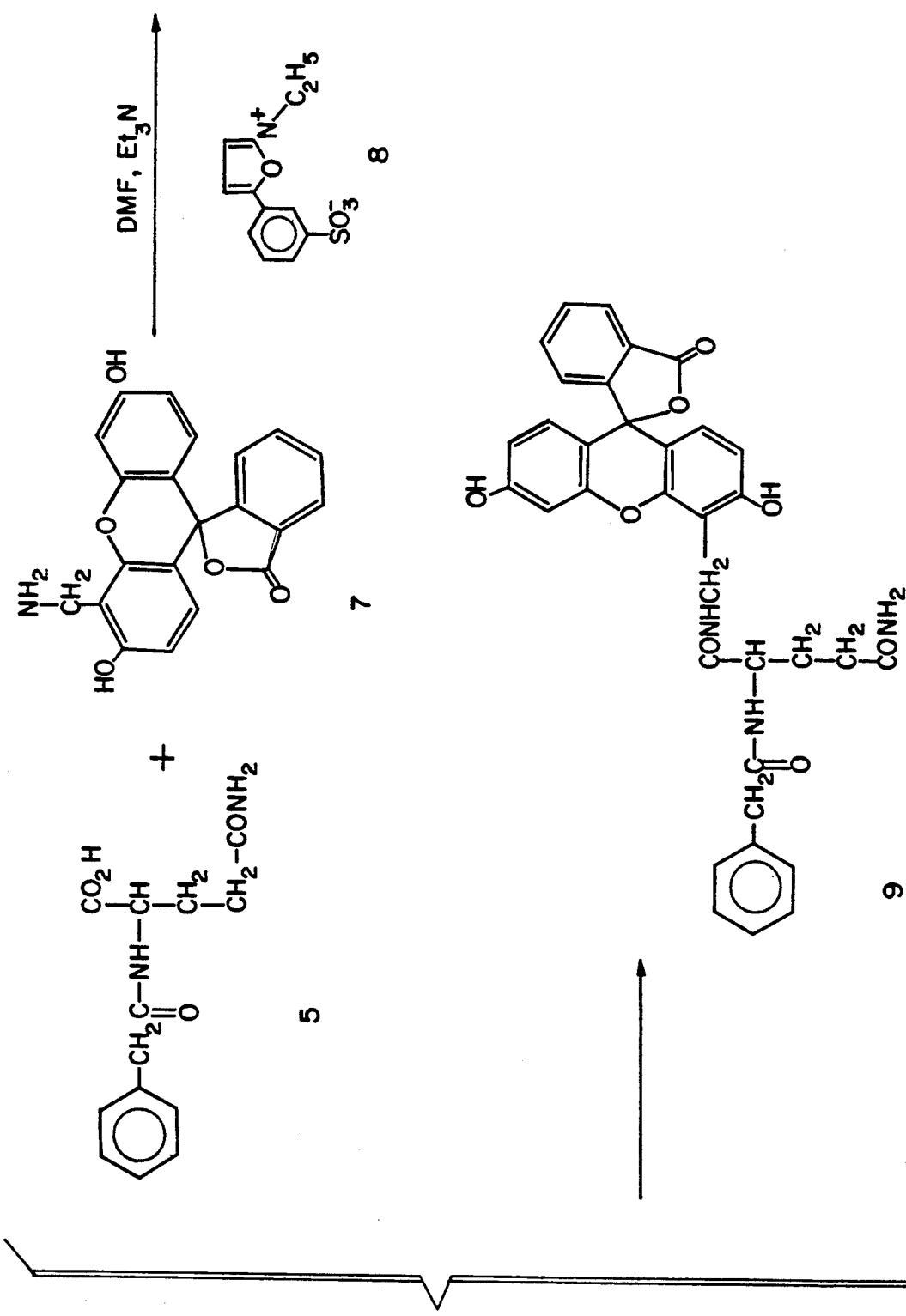
FIG. 3 illustrates the synthetic pathway for coupling PAG to aminomethylfluorescein (AMF) according to the method of the present invention.

As shown in Scheme III (FIG. 3), phenylacetylglutamine 5 (25 mg) from Example 1 was dissolved in dimethylformamide (500 μl), and 2-ethyl 5-phenylisoxazolium-3'-sulfonate 8 (26 mg) was added. The pH of the reaction mixture was adjusted to 9 with triethylamine. After 45 minutes, aminomethylfluorescein hydrochloride 7 (38 mg) was added, and reaction mixture was stirred for an additional 12 hours. After evaporation to dryness, the residue was dissolved in methanol and purified by preparative thin layer chromatography using reversed silica gel and water-methanol-acetic acid (40:60:0.4) as an eluent. The result was 40 mg of the desired PAG/AMF conjugate 9. Mass spectrum (FAB): 608 M+.

EXAMPLE 4

Coupling of Phenylacetylglutamine to Glycine t-Butylester

Phenylacetylglutamine (50 mg) from Example 1 was dissolved in anhydrous dimethylformamide (800 ul), and 2-ethyl 5 phenylisoxazolium -3' sulfonate (53 mg) was added. The reaction mixture was adjusted to pH 9 with triethylamine. After 90 minutes, glycine t-butylester hydrochloride (32 mg) was added, and the reaction mixture was stirred for additional 12 hours, evaporated to dryness and the residue was purified by preparative thin layer chromatography using ethyl acetate-methanol (90/10) as an eluent. Yield 63%; mp. 173°-175° C. Mass spectrum (DCl/NH$_3$/DIP): 395 (M+NH$_4$)+ (13%), 378 (M+H)+ (18%). 153 (100%).

This PAG-Glycine conjugate can in turn be linked to bovine serum albumin for raising antibodies to PAG, and to fluorescein for use as a tracer.

EXAMPLE 5

Antisera Production

Rabbits were initially immunized with 1 mg of the immunogen of Example 2 and subsequently boosted with 0.5 mg of the immunogen every 6 weeks. The animals were bled about 2 weeks after each boost. The bleeds were titrated to select the antisera collections demonstrating adequate binding and displacement at a reasonable dilution. A typical pool is diluted 1 to 8, has a binding of about 250 millipolarization (mP) unit and a displacement of about 150 mP's with a PAG solution containing 300 ug phenyl acetate equivalent per milliliter.

EXAMPLE 6

Illustrative Immunoassay a. Tracer Solution The tracer prepared according to Example 3 was dissolved in a solution containing sodium chloride 1.0, sodium azide (0.1 g), sodium thiosulfate (0.1 g), glycerol (25 ml), dimethylformamide (25 ml) and water (50 ml) such that the fluorescence intensity of the tracer solution was 5,000-6,000 units when 25 μl of the tracer solution was dissolved in 1,975 ul of the Buffer Solution below.

b. Popper Solution Tris (hydroxymethyl) aminomethane (0.12 g), sodium laurel sulfate (0.1 g) and sodium azide (0.01 g) were dissolved in water (100 ml).

c. Antisera Solution A solution was prepared by adding potassium phosphate monobasic (0.054 g), potassium phosphate dibasic (0.164 g), sodium azide (0.01 g), sodium chloride (0.9 g), and chicken egg albumin hydrolysate (1.0 g) to water (100 ml). The antisera of Example 5 was added to this solution such that its dilution was from 1 to 8 in the solution.

d. Artificial Urine An artificial urine was prepared by mixing urea (2.0 g), creatinine hydrochloride (0.20 g), sodium chloride (1.0 g), potassium sulfate (0.17 g), potassium phosphate dibasic (0.176 g), potassium phosphate dibasic (0.14 g), magnesium sulfate (0.12 g), sodium azide (0.10 g), sodium thiosulfate (0.1 g), and sodium hydroxide (to adjust pH to 7.3-7.5) in water (1.0 L). The artificial urine is used to prepare calibrators and controls.

Standard solutions of PAG (prepared according to Example 1) in artificial urine were prepared in the following concentrations (expressed in phenylacetic acid equivalents): 0, 25, 50, 100, 150 and 300 ug/ml.

An aliquot of each standard solution (0.5 μl) was mixed in a cuvette with antiserum (12.5 μl) and buffer solution (25 μl). After several minutes a fluorescent background reading was taken on an Abbott TDx fluorescence polarization instrument.

0.5 μl of each calibrator was again transferred to a cuvette, together with 12.5 μl of antiserum and 25 ul of the PAG/AMF tracer solution. After an incubation period of about three minutes, a final reading was taken and the PAG concentration values were stored as a standard curve, after subtracting the background readings for each calibrator.

Figure 4:
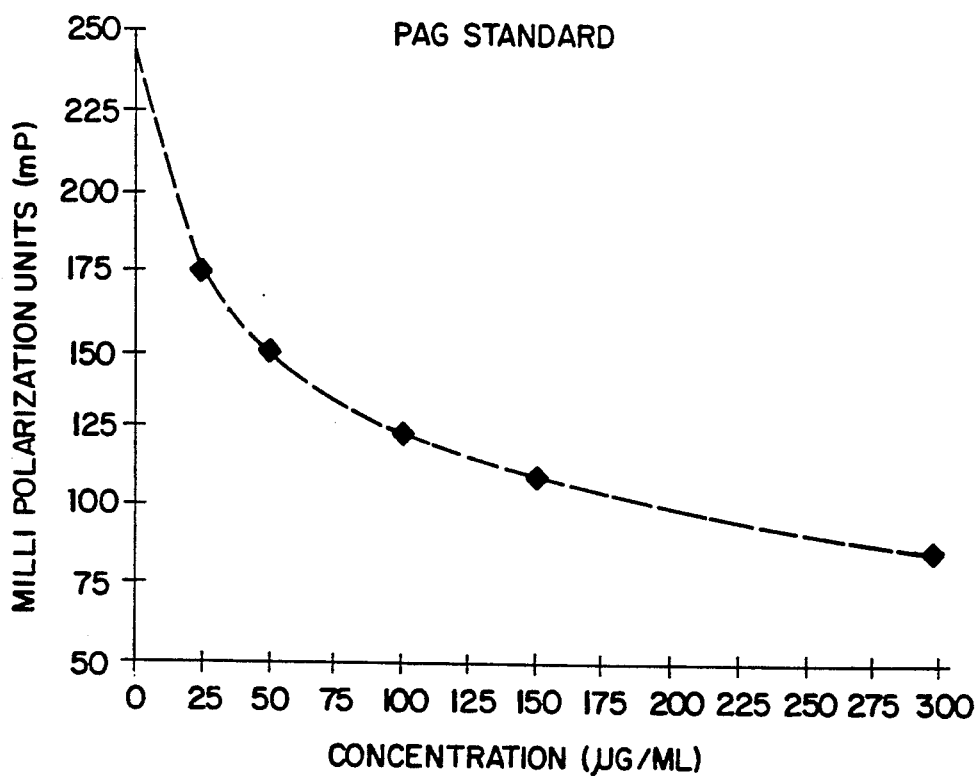
FIG. 4 is a graph which illustrates the results of an immunoassay employing the antibody, conjugate and method according to the present invention.

The results are shown in FIG. 4.

Actual urine samples are analyzed by mixing an aliquot (0.5 μl) of each sample in a cuvette with antiserum (12.5 μl) and buffer solution (25 μl), and taking a background fluorescence polarization reading. After the background reading, an aliquot (0.5 μl) of each sample is placed in a cuvette with antiserum (12.5 μl) and tracer (25 μl). After incubating the samples for three minutes, a final polarization reading for each sample was taken subtracting the background reading from the final reading in each instance to get a corrected value. The corrected values were compared with the standard curve above to get the PAG concentration in each sample.

EXAMPLE 7

This example illustrates the accuracy of the method of the FPIA of the present invention vis-a-vis the primary method currently in use, gas chromatography with MS detection (GC-MS).

GC-MS vs. FPIA (n=40)
Intercept=1.124
Slope=0.8935
Coefficient of correlation=0.9748.

Figure 5:
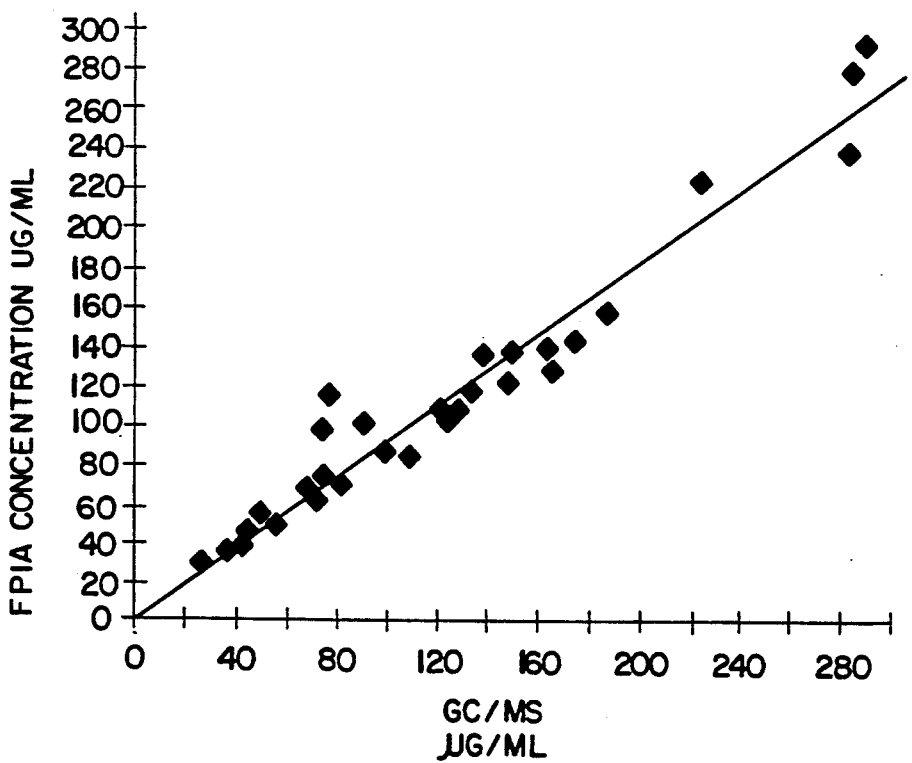
FIG. 5 is a graph which illustrates the accuracy of the method of the fluorscent polarization immunoassay of the present invention compared to gas chromatography with MS detection methods.

Although the GC/MS method measures total phenylacetic acid in the sample and the FPIA assay measures PAG (as phenyl acetic acid), the two methods correlate very closely (FIG. 5). This indicates that the urinary phenyl acetate secretion can be effectively and accurately measured by a FPIA urinary PAG assay.

It took 5 days to assay the 40 samples in this example by GC/MS since the method is very time consuming and labor intensive. But the same 40 samples took about thirty minutes to run by the FPIA method of this invention.

EXAMPLE 8

Standard Additional Recovery

This example, wherein three urine samples were spiked with PAG and the percentage of the spike detected in each instance was determined.

Four aliquots of each urine sample were spiked with PAG so that the following concentrations of added PAG were obtained in the aliquots of each sample: 150, 100, 50, 25 µg/ml phenylacetic acid equivalent.

A standard curve was prepared using calibrators comprised of PAG in artificial urine treated in the same fashion as the samples. The standard curve was stored in the instrument, and samples were compared to the curve.

The percentage of spiked PAG recovered in the spiked urine samples was determined by 1) subtracting the endogenous PAG (0 mg/ml spike) from the measured urine spike levels (i.e., adjusted concentration = concentration measured − endogenous PAG, as phenyl acetate (PA) equivalents), and 2) dividing by the target value of the PAG spike.

$$\% \text{ Recovery} = \frac{\text{Adjusted concentration}}{\text{Concentration of PA spiked}} \times 100$$

The results are shown in Table I. As shown in Table I, the recovery in each instance exceeds 92%.

TABLE I

Recovery From Spiked Human Urine Samples

| Spiked Concentration | Sample 1 | | Sample 2 | | Sample 3 | |
| --- | --- | --- | --- | --- | --- | --- |
| | Adjusted Conc. | % Recovery | Adjusted Conc. | % Recovery | Adjusted Conc. | % Recovery |
| 25.00 | 24.49 | 97.9 | 23.21 | 92.4 | 23.43 | 93.7 |
| 50.00 | 47.58 | 95.2 | 47.18 | 94.4 | 47.52 | 95.04 |
| 100.00 | 95.2 | 95.2 | 93.5 | 93.5 | 95.6 | 95.6 |
| 150.00 | 146.47 | 97.6 | 138.88 | 92.6 | 146.75 | 97.8 |

EXAMPLE 9

This example illustrates the characteristics of the novel antisera of the present invention. With the procedure described in Example 5, rabbits were inoculated and boosted with above described immunogen (Example 2). The anti-PAG antisera produced was observed to have very rapid binding and displacement kinetics. The incubation time for binding and displacement is only about three minutes. The adequacy of three minute incubation was tested by assaying a single sample in 20 replicates in groups of five in two trials (Trials I and II, Table II). The test was carried out at two levels; A for 0 µg/ml PAG and L for 30 µg/ml PAG. The A level was used to test the binding kinetics of the tracer (Example 3) and the L level was used to study the kinetics of the displacement of the tracer by PAG (Example 1). The data are shown in Table II. The average polarizations for each group stayed essentially the same, and standard deviations within groups of five were less than 1 mp or much less than 1%. The results indicate that because of very rapid kinetics of the binding, equilibrium is reached very quickly and any incidental time differences (e.g. time differences due to machine operation) among these samples (1 through 20) had no significant effect on the results. Accordingly, a three minute incubation time achieves repeatable, accurate results.

TABLE II

| | | Mixing/Timing | | | |
| --- | --- | --- | --- | --- | --- |
| | | Trial I | | Trial II | |
| | | A | L | A | L |
| Standard dev. within groups of 5 (mP's) | Group | | | | |
| | 1 | 1.06 | 0.75 | 0.59 | 0.62 |
| | 2 | 0.27 | 0.25 | 0.62 | 0.73 |
| | 3 | 0.73 | 0.49 | 0.55 | 0.57 |
| | 4 | 1.16 | 0.49 | 0.88 | 0.54 |
| Mean mP Difference between groups of 5 reps. | Group Pairs | | | | |
| | 1 & 2 | 0.07 | 0.13 | 0.18 | 0.11 |
| | 1 & 3 | 0.04 | 0.20 | 0.39 | 0.58 |
| | 1 & 4 | 0.20 | 0.24 | 0.44 | 0.32 |
| | 2 & 3 | 0.03 | 0.07 | 0.21 | 0.69 |
| | 2 & 4 | 0.13 | 0.11 | 0.26 | 0.43 |
| | 3 & 4 | 0.16 | 0.04 | 0.05 | 0.26 |

A = 0 PAG/m/
L = 25 µg PAG asPAA/m/

EXAMPLE 10

The uniqueness of the antibody was established by studying cross reactivity of some structurally related compounds with PAG in the Abbott Laboratories TDx assay. Even at levels of up to 1000 µg/ml of these related compounds no cross reactivity was observed as shown in Table III.

For each compound, solutions containing various concentrations (from 0.1 to 1,000 mg/ml) were prepared. Each solution was then analyzed as one would perform a FPIA assay for PAG. If any detectable concentration were observed, that would have been indicative of a cross-reactivity of the compound with the PAG antibody. Any cross-reactivity is, of course, undesirable.

TABLE III

| | Cross-Reactivity | | | | |
| --- | --- | --- | --- | --- | --- |
| | Concentration Levels (mg/ml) | | | | |
| Compound | 0.1 | 1.0 | 10.0 | 100.0 | 1000.0 |
| Beta-PEA | ND* | ND* | ND* | ND* | 0.57 |
| 5HIAA | ND* | ND* | ND* | ND* | ND* |
| D, L-DOPA | ND* | ND* | ND* | ND* | ND* |
| Tryptamine | ND* | ND* | ND* | ND* | ND* |
| 3, 4-DihyPAA | ND* | ND* | ND* | ND* | ND* |
| MHPG | ND* | ND* | ND* | ND* | ND* |
| p-HyPAA | ND* | ND* | ND* | ND* | ND* |
| m-HyPAA | ND* | ND* | ND* | ND* | ND* |
| (R) 2PAA | ND* | ND* | ND* | ND* | ND* |
| (S) 2PPA | ND* | ND* | ND* | ND* | ND* |
| PAA | No cross-reactivity | | | | |
| Glutamine | No cross-reactivity | | | | |

*no cross-reactivity detected

We claim:

1. An antibody specific for phenylacetylglutamine raised against an immunogen of the formula:

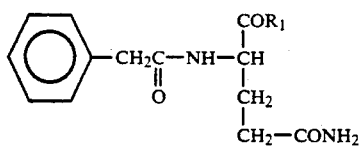

wherein $R_1$ is a poly(amino acid) carrier.

2. The antibody according to claim 1 wherein $R_1$ is bovine serum albumin.

3. Antisera specific for phenylacetylglutamine prepared by 1) innoculating a mammal with an immunogen of the formula:

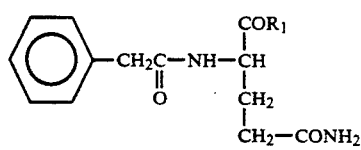   I wherein $R_1$ is a poly(amino acid) carrier.

4. The antisera of claim 3 wherein said mammal is a rabbit.

5. The antisera of claim 4 wherein $R_1$ is bovine serum albumin.

6. An immunoassay reagent comprising an antibody according to claim 1, and labeled phenylacetylglutamine (PAG).

7. An immunoassay comprising antisera according to claim 3, and labeled phenylacetylglutamine (PAG).

8. The immunoassay reagent of claim 7 wherein said labelled PAG comprises a conjugate of fluorescein and phenylacetylglutamine.

9. A conjugate for use in an immunoassay for PAG, comprising

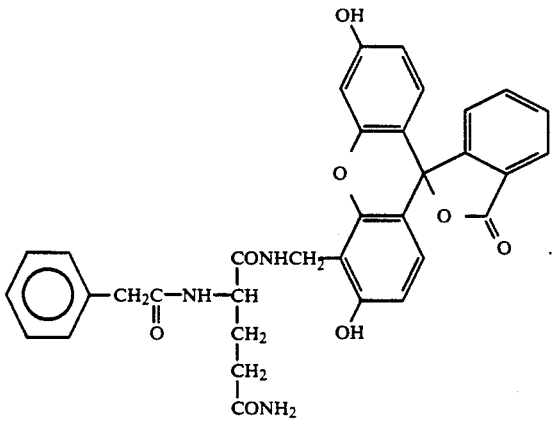

10. A method of performing an immunoassay for PAG in a sample, comprising:
 a) exposing the sample to an antibody according to claim 1;
 b) exposing the sample to a conjugate of claim 9; and
 c) measuring the fluorescence polarization of the sample as an indication of the amount of PAG in the sample.

* * * * *

UNITED STATES PATENT AND TRADEMARK OFFICE
CERTIFICATE OF CORRECTION

PATENT NO. : 5,100,807

DATED : Mar. 31, 1992

INVENTOR(S) : Maciej B. Adamczyk, Hossein A. Ghanbari, Donald D. Johnson

It is certified that error appears in the above-identified patent and that said Letters Patent is hereby corrected as shown below:

Column 2, line 68
Delete "plan" and insert --plane--

Column 4, line 19
Delete "4" and insert --$\underline{4}$--

Column 4, line 22
Delete "2" and insert --$\underline{2}$--

Column 4, line 25
Delete "3" and insert --$\underline{3}$--

Column 4, line 27
Delete "3" and insert --$\underline{3}$--

Column 4, line 29
Delete "4" and insert --$\underline{4}$--

Column 4, line 32
Delete "5" and insert --$\underline{5}$--

Column 4, line 42
Delete "5" and insert --$\underline{5}$--

Column 4, line 44
Delete "5" and insert --$\underline{5}$--

Column 4, line 49
Delete "6" and insert --$\underline{6}$--

UNITED STATES PATENT AND TRADEMARK OFFICE
CERTIFICATE OF CORRECTION

PATENT NO. : 5,100,807              Page 2 of 3

DATED : Mar. 31, 1992

INVENTOR(S) : Maciej B. Adamczyk, Hossein A. Ghanbari, Donald D. Johnson

It is certified that error appears in the above-identified patent and that said Letters Patent is hereby corrected as shown below:

Column 4, line 63
Delete "6" and insert --$\underline{6}$--

Column 5, line 3
Delete "10" and insert --$\underline{10}$--

Column 5, line 9
Delete "5" and insert --$\underline{5}$--

Column 5, line 12
Delete "8" and insert --$\underline{8}$--

Column 5, line 15
Delete "7" and insert --$\underline{7}$--

Column 5, line 21
Delete "9" and insert --$\underline{9}$--

UNITED STATES PATENT AND TRADEMARK OFFICE
CERTIFICATE OF CORRECTION

PATENT NO. : 5,100,807
DATED : March 31, 1992
INVENTOR(S) : Maciej B. Adamczyk, Hossein A. Ghanbari, Donald D. Johnson It is certified that error appears in the above-indentified patent and that said Letters Patent is hereby corrected as shown below:

Column 5, line 38
Delete "(18%)." and insert --(18%),--

Column 5, line 63
Delete "1.0." and insert --(1.0g),--

Signed and Sealed this

Fourteenth Day of September, 1993

Attest:

BRUCE LEHMAN

*Attesting Officer*    Commissioner of Patents and Trademarks